United States Patent
Masculo et al.

(10) Patent No.: US 11,769,077 B2
(45) Date of Patent: Sep. 26, 2023

(54) METHODS AND SYSTEMS TO CHARACTERIZE THE USER OF A PERSONAL CARE DEVICE

(71) Applicant: KONINKLIJKE PHILIPS N.V., Eindhoven (NL)

(72) Inventors: Felipe Maia Masculo, Eindhoven (NL); Vincent Jeanne, Migne Auxances (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 441 days.

(21) Appl. No.: 16/755,319

(22) PCT Filed: Oct. 10, 2018

(86) PCT No.: PCT/EP2018/077603
§ 371 (c)(1),
(2) Date: Apr. 10, 2020

(87) PCT Pub. No.: WO2019/072917
PCT Pub. Date: Apr. 18, 2019

(65) Prior Publication Data
US 2021/0201194 A1 Jul. 1, 2021

Related U.S. Application Data

(60) Provisional application No. 62/571,842, filed on Oct. 13, 2017.

(51) Int. Cl.
*G16H 20/30* (2018.01)
*G06N 20/00* (2019.01)
(Continued)

(52) U.S. Cl.
CPC ............. *G06N 20/00* (2019.01); *G16H 40/40* (2018.01); *G16H 40/67* (2018.01); *G16H 50/70* (2018.01)

(58) Field of Classification Search
CPC ........ G06N 20/00; G16H 40/40; G16H 40/67; G16H 50/70
See application file for complete search history.

(56) References Cited

U.S. PATENT DOCUMENTS 6,536,068 B1 3/2003 Yang et al.
11,006,742 B2 5/2021 Jeanne et al.
(Continued)

FOREIGN PATENT DOCUMENTS

CN 204581569 U 8/2015
CN 105662630 A 6/2016
(Continued)

OTHER PUBLICATIONS

International Search Report and Written Opinion, International Application No. PCT/EP2018/077603, dated Jan. 23, 2019.

*Primary Examiner* — Shahid Merchant
*Assistant Examiner* — Benjamin L. Hanks

(57) ABSTRACT

A method (300) for identifying a characteristic of a user of a personal care device (10) comprising a sensor (28), a controller (30), and a database (34), comprising the steps of: training (320) the device with training data, comprising the steps of: (i) obtaining (322) sensor data for at least one personal care session for each of at least two different users; (ii) extracting (324), via an extraction module, a plurality of features from each of the personal care sessions; and (iii) training (328), using the extracted features, a classifier to identify a characteristic of each of the at least two different users of the device; obtaining (330) sensor data for at least part of a new personal care session; extracting (340) a plurality of features from the sensor data for the new personal care session; and identifying (360), using the trained classifier, a characteristic of the user of the device.

20 Claims, 4 Drawing Sheets

(51) Int. Cl.
*G16H 40/67* (2018.01)
*G16H 40/40* (2018.01)
G16H 50/70 (2018.01)

(56) References Cited

U.S. PATENT DOCUMENTS

| | | |
|---|---|---|
| 2003/0101526 A1* | 6/2003 | Hilscher .............. A61C 17/221 |
| | | 15/22.1 |
| 2007/0265495 A1 | 11/2007 | Vayser |
| 2008/0020351 A1 | 1/2008 | Hilscher |
| 2009/0262072 A1 | 10/2009 | Chen |
| 2009/0262073 A1* | 10/2009 | Rigazio ............ H04N 21/42208 |
| | | 345/158 |
| 2015/0127371 A1 | 5/2015 | Dykes et al. |
| 2016/0143718 A1 | 5/2016 | Serval |
| 2016/0235357 A1 | 8/2016 | Ohmer |
| 2017/0035327 A1 | 2/2017 | Yuen et al. |
| 2017/0069083 A1* | 3/2017 | Vetter .................. A61B 5/1128 |
| 2019/0083215 A1 | 3/2019 | Serval |
| 2020/0179089 A1* | 6/2020 | Serval .................... G06N 20/00 |

FOREIGN PATENT DOCUMENTS

| | | |
|---|---|---|
| CN | 106820563 A | 6/2017 |
| DE | 10224043 A1 | 12/2003 |
| KR | 1759898 B1 | 7/2017 |
| WO | 02071972 A1 | 9/2002 |

\* cited by examiner

METHODS AND SYSTEMS TO CHARACTERIZE THE USER OF A PERSONAL CARE DEVICE

This application is the U.S. National Phase application under 35 U.S.C. § 371 of International Application No. PCT/EP2018/077603, filed on 10 Oct. 2018, which claims the benefit of U.S. Provisional Application No. 62/571,842, filed 13 Oct. 2017. These applications are hereby incorporated by reference herein.

FIELD OF THE INVENTION

The present disclosure is directed generally to methods and systems for identifying or characterizing the user of a personal care device.

BACKGROUND

To facilitate proper use and operation of personal care devices, some devices contain one or more sensors that measure relevant information about the user's operating characteristics and behavior and use it to provide feedback to the user. The feedback can be provided to the user in real-time or after the end of an operating session. However, for some equipment, it is common for multiple users to share a device, replacing components that contact the user's body. In this circumstance, the system must be able to match each use session to a specific user profile in order to provide personalized feedback for the correct user. In the case of real-time feedback, the user may have access to a smartphone during the operating session and can be identified by the app since every user typically has a separate user account. For some use scenarios, such as post-session feedback, the system may not be able to rely on an external device to identify the user, and thus will not know the identity of the user. Indeed, it is currently impossible to identify the user of the device without external information provided by the user. As a result, it may not be possible to provide personalized use session feedback to the proper user.

Accordingly, there is a continued need in the art for methods and systems that accurately identify a user and/or a characteristic of a user of a personal care device without requiring an external identifier of the user.

SUMMARY OF THE INVENTION

The present disclosure is directed to inventive methods and systems for identifying or characterizing the user of a personal care device. Applied to a personal care device, for example, the inventive methods and systems enable identification of the user and thus allow for feedback personalized to the identified user. The system obtains sensor data for a plurality of personal care sessions for two or more users of the personal care device, and extracts features from each of the personal care sessions in order to train a classifier to identify one or more characteristics of each of the two or more users of the device. Once the device is trained, the system obtains sensor data for a new personal care session, extracts features from the new personal care session, and uses the classifier to identify the user or a characteristic of the user. Once the user is identified, the device can utilize the information to modify a parameter of the personal care device, provide feedback to the user, or continue to train the device, among other uses.

Generally in one aspect, a method for identifying a characteristic of a user of a personal care device comprising a sensor, a controller, and a database is provided. The method includes the steps of: (i) training the personal care device with training data, comprising the steps of: obtaining, via the sensor, sensor data for at least one personal care session for each of at least two different users of the personal care device; extracting, via an extraction module of the processor, a plurality of features from each of the personal care sessions; and training, using the extracted plurality of features, a classifier to identify a characteristic of each of the at least two different users of the personal care device; (ii) obtaining, via the sensor, sensor data for at least part of a new personal care session initiated by one of the at least two different users of the personal care device; (iii) extracting a plurality of features from the sensor data for the new personal care session; and (iv) identifying, using the trained classifier, a characteristic of the user of the personal care device.

According to an embodiment, the method further includes the step of reducing, using a dimensionality reduction process, the number of extracted plurality of features from one or more of the personal care sessions, prior to the training step.

According to an embodiment, the method further includes the step of reducing, using a dimensionality reduction process, the number of extracted plurality of features from the new personal care session, prior to the identifying step.

According to an embodiment, the method further includes the step of associating at least some of the sensor data obtained during the new personal care session with the identified characteristic of the user.

According to an embodiment, the method further includes the step of providing, based on the identified characteristic, feedback to the user or a third party.

According to an embodiment, the method further includes the step of modifying, based on the identified characteristic, a parameter of the personal care device.

According to an embodiment, the identified characteristic of the user is an identification of the user. According to an embodiment, the identified characteristic of the user is an operating or use parameter of the user.

According to an embodiment, the classifier comprises a predictive model.

According to an embodiment, the sensor is an inertial measurement unit.

According to an aspect is a personal care device configured to identify a characteristic of a user of the device. The personal care device includes a sensor configured to obtain sensor data for a plurality of personal care sessions, and further includes a controller comprising a training module and a classifier, the training module configured to: (i) receive, from the sensor, sensor data for at least one personal care session for each of at least two different users of the personal care device; (ii) extract, via an extraction module of the processor, a plurality of features from each of the personal care sessions; and (iii) train, using the extracted plurality of features, a classifier to identify a characteristic of each of the at least two different users of the personal care device; where the controller is further configured to receive, from the sensor, sensor data for at least part of a new personal care session initiated by one of the at least two different users of the personal care device, and extract a plurality of features from the sensor data for the new personal care session; and wherein the classifier is configured to identify, using the extracted plurality of features from the new personal care session, a characteristic of the user of the personal care device.

According to an embodiment, the controller further comprises a dimensionality reduction module configured to reduce the number of extracted plurality of features from one or more of the personal care sessions prior to the identifying step, and/or configured to reduce the number of extracted plurality of features from the new personal care session prior to the identifying step.

According to an embodiment, the controller is further configured to provide, based on the identified characteristic, feedback to the user. According to an embodiment, the controller is further configured to modify, based on the identified characteristic, a parameter of the personal care device.

As used herein for purposes of the present disclosure, the term "controller" is used generally to describe various apparatus relating to the operation of a stream probe apparatus, system, or method. A controller can be implemented in numerous ways (e.g., such as with dedicated hardware) to perform various functions discussed herein. A "processor" is one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media (generically referred to herein as "memory," e.g., volatile and non-volatile computer memory). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present disclosure discussed herein. The terms "program" or "computer program" are used herein in a generic sense to refer to any type of computer code (e.g., software or microcode) that can be employed to program one or more processors or controllers.

The term "user interface" as used herein refers to an interface between a human user or operator and one or more devices that enables communication between the user and the device(s). Examples of user interfaces that may be employed in various implementations of the present disclosure include, but are not limited to, switches, potentiometers, buttons, dials, sliders, track balls, display screens, various types of graphical user interfaces (GUIs), touch screens, microphones and other types of sensors that may receive some form of human-generated stimulus and generate a signal in response thereto.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of a method and system that utilizes sensor data to identify the user of a device in order to provide feedback. More generally, Applicant has recognized and appreciated that it would be beneficial to provide a system that identifies or characterizes the user of a personal care device. Accordingly, the methods and systems described or otherwise envisioned herein provide a personal care device configured to obtain sensor data for a plurality of personal care sessions for two or more users of the personal care device, wherein the personal care session is a brushing session, shaving session, cleaning session, or any other personal care session. The device extracts features from each of the personal care sessions in order to train a classifier to identify one or more characteristics of each of the two or more users of the device. Once the device is trained, the system obtains sensor data for a new personal care session, extracts features from the new personal care session, and uses the classifier to identify the user or a characteristic of the user. According to an embodiment, the device can utilize the information to modify a parameter of the personal care device, provide feedback to the user, or continue to train the device, among other uses.

The embodiments and implementations disclosed or otherwise envisioned herein can be utilized with any personal care device. Examples of suitable personal care devices include an electric toothbrush, an electric flossing device, an oral irrigator, a tongue cleaner, a shaver, a skin care device, or other personal care device. However, the disclosure is not limited to these enumerated devices, and thus the disclosure and embodiments disclosed herein can encompass any personal care device.

Figure 1:
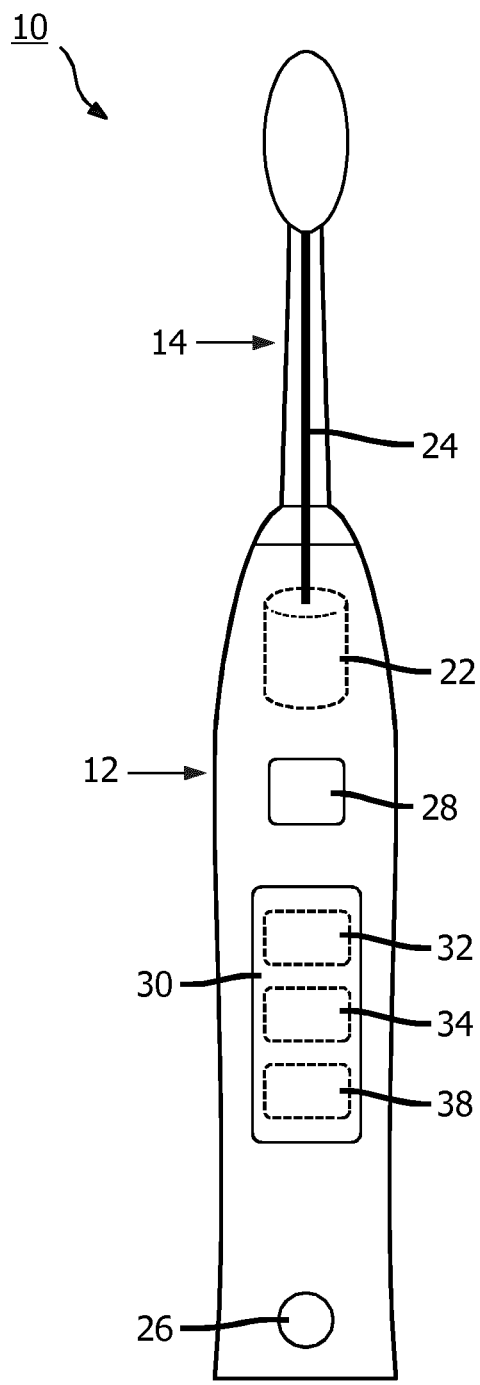
FIG. 1 is a representation of a personal care device, in accordance with an embodiment.

Referring to FIG. 1, in one embodiment, a personal care device 10 is provided that includes a handle or body portion 12 and a head member 14, which typically is the portion that operates on the human body. The head member, or a portion of it, may be removable, such as for different operations, for replacement when worn, or so that different users can attach a personalized component.

The body portion 12 typically comprises a housing, at least a portion of which is hollow, to contain components of the personal care device. The body portion 12 can comprise a drivetrain assembly with a motor 22 for generating movement, and a transmission component or drivetrain shaft 24, for transmitting the generated movements to head member 14. The personal care device may have a power supply (not shown), which can comprise one or more rechargeable batteries, not shown, which can, for example, be electrically charged in a charging holder in which personal care device 10 is placed when not in use. Body portion 12 is further provided with a user input 26 to activate and de-activate the drivetrain. The user input 26 allows a user to operate the personal care device 10, for example to turn the device on and off. The user input 26 may, for example, be a button, touch screen, or switch.

Personal care device 10 includes one or more sensors 28 configured to obtain sensor data. Sensor 28 is shown in FIG. 1 within body portion 12, but may be located anywhere within the device, including for example within head member 14, or elsewhere within or on the device. According to an embodiment, sensor 28 is configured to provide readings of six axes of relative motion (three axes translation and three axes rotation), using for example a 3-axis gyroscope and a 3-axis accelerometer. As another example, sensor 28 is configured to provide the readings of nine axes of relative motion using, for example, 3-axis gyroscope, a 3-axis accelerometer, and a 3-axis magnetometer. Other sensors may be utilized either alone or in conjunction with these sensors, including but not limited to a gyroscope, a capacitive sensor, a camera, a photocell, and other types of sensors. Many different types of sensors could be utilized, as described or otherwise envisioned herein. According to an embodiment, sensor 28 is configured to generate information indicative of the acceleration and angular orientation of personal care device 10. The sensor may comprise two or more sensors 28 that function together as the 6-axis or a 9-axis spatial sensor system.

Sensor data generated by sensor 28 is provided to a controller 30. According to one embodiment, sensor 28 is integral to controller 30. Controller 30 may be formed of one or multiple modules, and is configured to operate the personal care device 10 in response to an input, such as input obtained via user input 26. Controller 30 can comprise, for example, a processor 32 and a memory or database 34. Processor 32 may take any suitable form, including but not limited to a microcontroller, multiple microcontrollers, circuitry, a single processor, or plural processors. Memory or database 34 can take any suitable form, including a non-volatile memory and/or RAM. The non-volatile memory may include read only memory (ROM), a hard disk drive (HDD), or a solid state drive (SSD). The memory can store, among other things, an operating system. The RAM is used by the processor for the temporary storage of data. According to an embodiment, an operating system may contain code which, when executed by controller 30, controls operation of the hardware components of personal care device 10. According to an embodiment, connectivity module 38 transmits collected sensor data, and can be any module, device, or means capable of transmitting a wired or wireless signal, including but not limited to a Wi-Fi, Bluetooth, near field communication, and/or cellular module.

Figure 2:
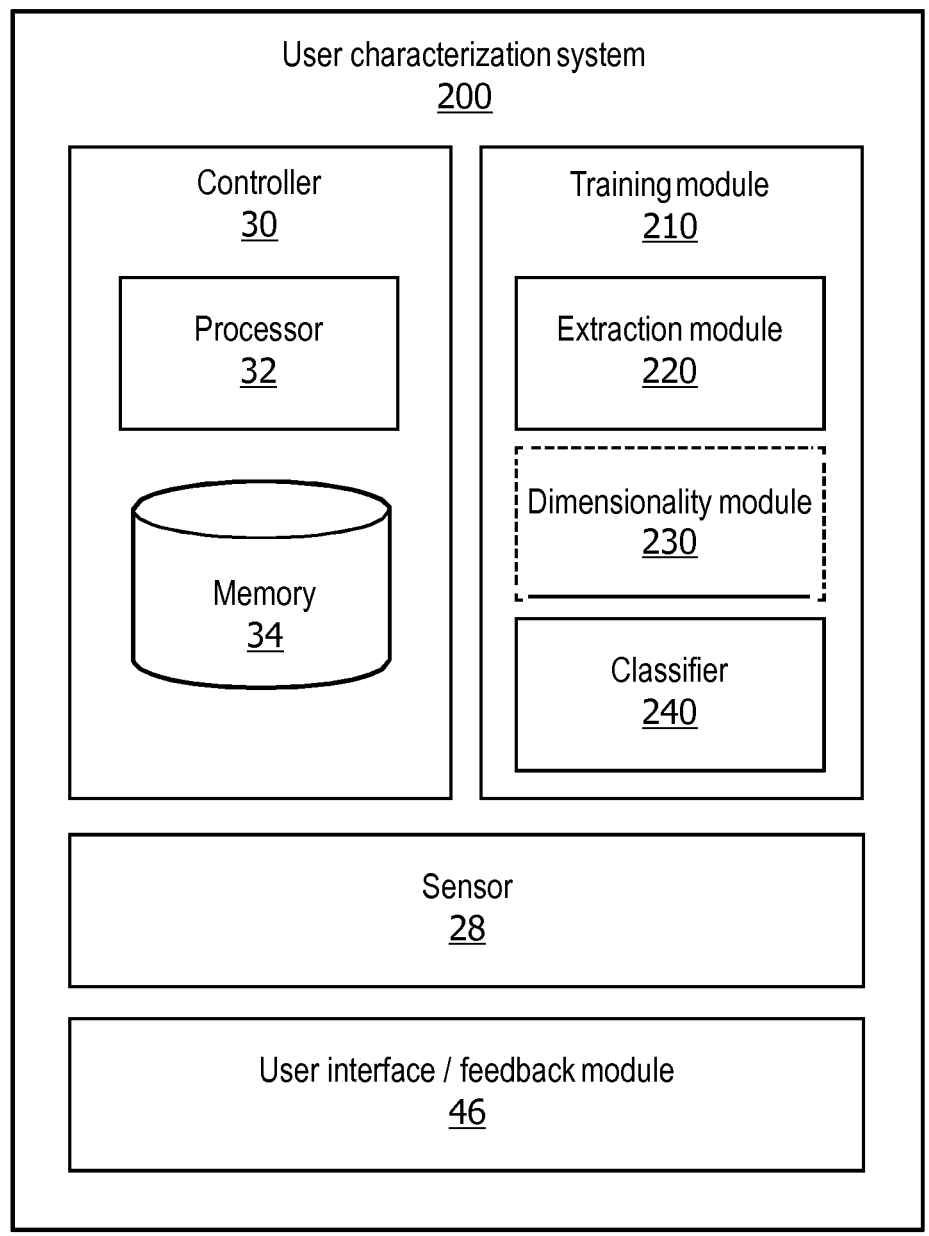
FIG. 2 is a schematic representation of a personal care system, in accordance with an embodiment.

Referring to FIG. 2, in one embodiment, is a user characterization system 200. User characterization system 200 is an embodiment of personal care device 10, which can be any of the personal care device embodiments disclosed or otherwise envisioned herein. According to another embodiment, user characterization system 200 can be implemented in two or more devices. For example, one or more of the modules or components of user characterization system 200 can be implemented in a remote device such as a smartphone, tablet, wearable device, computer, or other computer.

The user characterization system includes a controller 30 comprising a processor 32 and a memory 34. The user characterization system also comprises a sensor 28 configured to obtain information about an angle, movement, or other parameter of the device or the user. The user characterization system also includes a training module 210, an extraction module 220, a dimensionality module 230, and a classifier 240. The extraction module, classifier, and dimensionality module may or may not be a component or element of the training module. The user characterization system optionally includes a user interface 46, which provides information to the user. User interface 46 can be or can comprise a feedback module that provides feedback to the user via a haptic signal, audio signal, visual signal, and/or any other type of signal.

According to an embodiment, sensor 28 is a sensor such as an accelerometer, gyroscope, or any other type of sensor suitable for or configured to obtain sensor data about a position, movement, angle, or other physical parameter of the device. According to an embodiment, sensor 28 is configured to generate information indicative of the acceleration and angular orientation of personal care device 10. Sensor data generated by sensor 28 can be provided to controller 30 or any other component of the device or system, including an external device or application.

According to an embodiment, extraction module 220 is a component of the device, and/or a module or element of controller 30 or training module 210. The extraction module is configured, designed, or programmed to extract one or more features from a feature vector from the sensor data using signal processing. These features provide information that vary from one user to another and therefore can be used for identification.

According to an embodiment, dimensionality module 230 is a component of the device, and/or a module or element of controller 30 or training module 210. The optional dimensionality module is configured, designed, or programmed to reduce the number of features extracted by extraction module 220. The number of features extracted at the feature extraction step can be very large, which may lead to poor performance of predictive models. According to an embodiment, therefore, the dimensionality module can estimate a dimensionality reduction matrix which can be used to reduce the total number of features that are used to train the predictive model.

According to an embodiment, classifier 240 is a component of the device, and/or a module or element of controller 30 or training module 210. The classifier is trained with data from the extraction module and/or dimensionality module to identify a user of the personal care device, and/or a characteristic of the user of the device. Once the classifier is trained, it is configured, designed, or programmed to utilize new sensor data to determine to which user the use session belongs.

According to an embodiment, training module 210 is a component of the device, and/or a module or element of controller 30. The training module is configured to train the classifier with training data obtained by the sensor and processed by the extraction module and/or dimensionality module, as described or otherwise envisioned herein.

Figure 3:
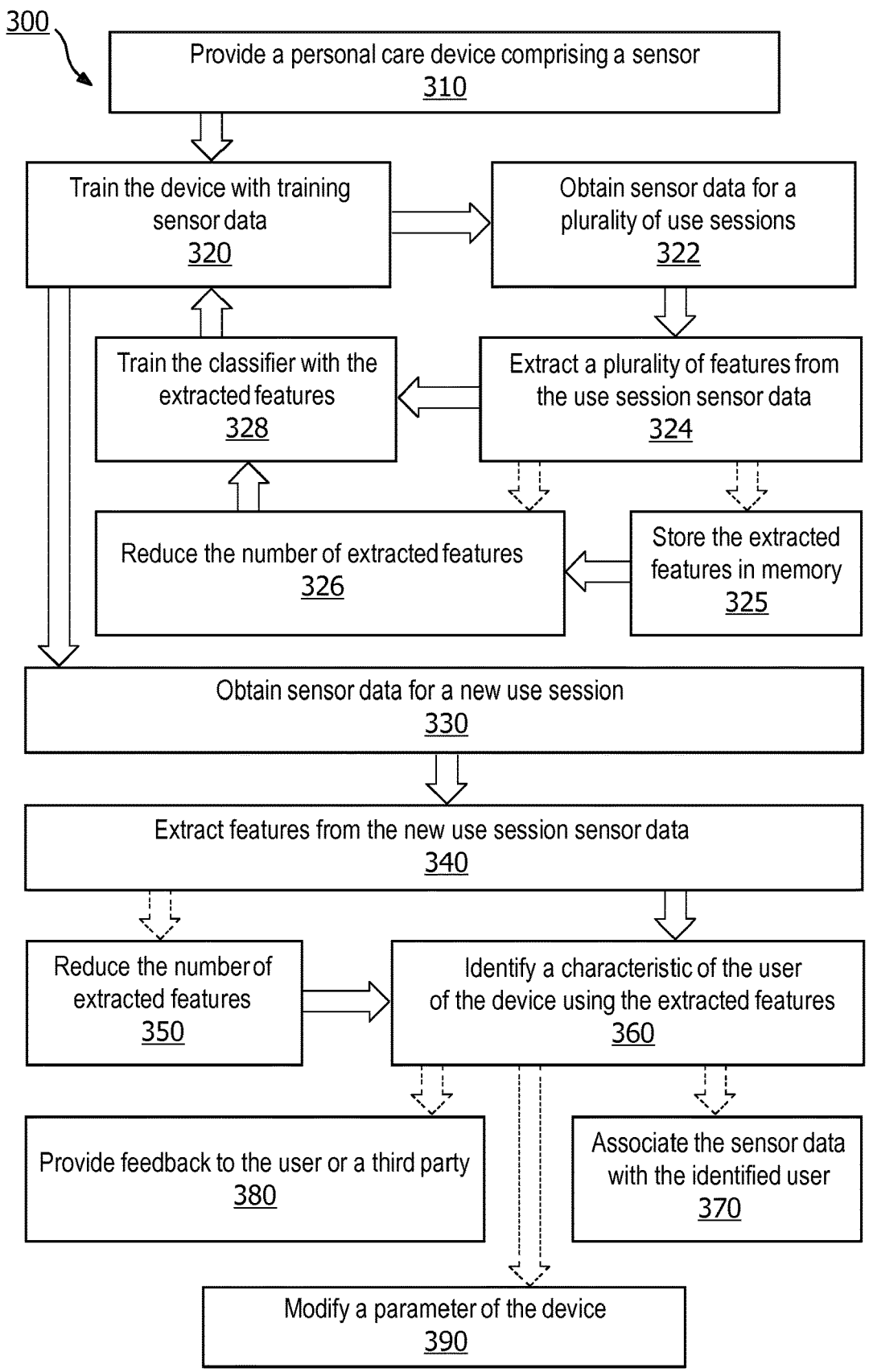
FIG. 3 is a flowchart of a method for characterizing the user of a personal care device, in accordance with an embodiment.

Referring to FIG. 3, in one embodiment, is a flowchart of a method 300 for identifying or characterizing the user of a personal care device. The method takes advantage of the fact that every user has a unique op pattern or technique. For example, some aspects of the user's operating technique such as typical device orientations and motion patterns can be measured with one or more sensors present in the device, and this information can be used to identify the user within a group of people such as a family.

According to an embodiment, the method comprises two phases, a training phase and a deployment phase. In the training phase, data from a number of use sessions is collected from every user that uses the same personal care device in order to create a predictive model. During this phase the users identify themselves so that their identity may be associated with the collected data. For example, the users may identify themselves using an external device or software application, or any other identification method. In the deployment phase, once a predict model has been generated in the training phase, the model is utilized to automatically identify the user. According to another embodiment, the identification of the user can be obtained, for example, by requesting that the user connect the device to an app, or by identifying the associated head, such as with an RFID tag in the head, if one is present.

According to an embodiment, every step in both the training and the deployment phases are performed by the personal care device. In an alternative embodiment, the steps of the method are distributed between the personal care device and a second device in communication with the personal care device, such as a smartphone, computer, server, or other device.

In step 310 of the method, a personal care device 10 is provided. Personal care device 10 can be any of the devices described or otherwise envisioned herein. For example, personal care device 10 may comprise a body handle or body portion 12, a head member 14, a motor 22, a user input 26, and a controller 30 with processor 32. The personal care device also includes a sensor 28 such as an accelerometer and/or gyroscope.

At step 320 of the method, the personal care device is trained with training sensor data as described or otherwise envisioned herein. According to an embodiment, training the personal care device to identify a user or a characteristic of a user comprises one or more of steps 322 through 328, which may be repeated numerous times, including during the deployment phase.

At step 322 of the method, the personal care device obtains sensor data for at least one personal care session for each of the users of the device. Typically, the personal care device obtains sensor data for a plurality of personal care sessions for each user. According to an embodiment, the more training sessions that are analyzed, the more training data is used to train the classifier, and the better the classifier is able to identify the user. The number of training sessions needed may be at least partially dependent upon the number of users of the device.

According to an embodiment, the personal care device or a component of the device such as the controller and/or training module determines the number of personal care sessions necessary to reliably identify the user of the device during the deployment stage. According to an embodiment, the number of personal care sessions necessary to train the classifier may be determined based on the number of user of the device. Accordingly, the user may input information to the device or system indicating the expected number of users of the device, and the device may be programmed or otherwise configured to obtain training data for a predetermined number of personal care sessions for each user based on the provided information. According to another embodiment, the number of personal care sessions necessary to train the classifier may be determined based on self-determination of accuracy by the device. For example, the device may perform an internal estimate of accuracy, or determine a confidence in a classification performed by the classifier. As just one example, the device may compare a prediction or classification to an actual identification of the user provided during either the training or the deployment stage, and based on that cross-validation, may determine either that additional training sessions are necessary, or that the classifier is sufficiently prepared for the deployment stage.

At step 324 of the method, the extraction module extracts a plurality of features from each of the personal care sessions. According to embodiment, discriminant features are extracted from the sensor data for every use session recorded by the device. The choice of features depends on the sensors present in the device. For example, the device may contain at least an inertial measurement unit, which may be composed of an accelerometer, and/or gyroscope, and/or magnetometer.

Figure 4:
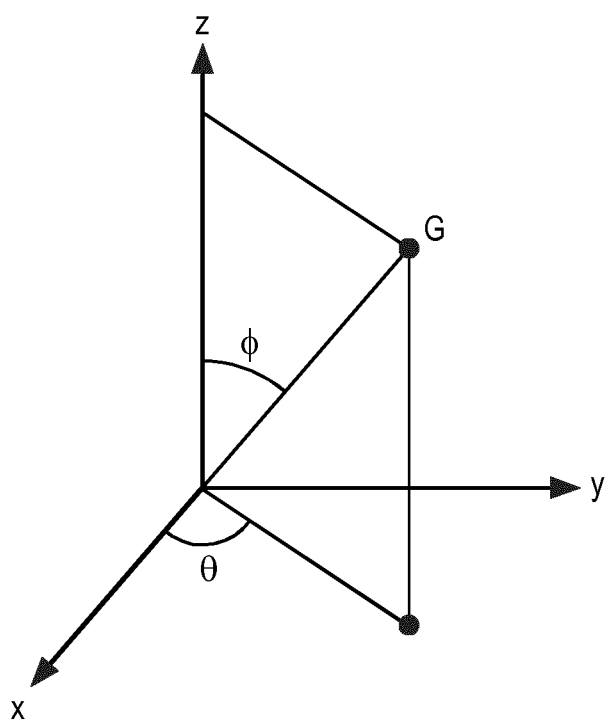
FIG. 4 is a schematic representation of angles representing the orientation of a personal care device with regard to gravity, in accordance with an embodiment.

According to an embodiment, several features can be extracted from the sensor. For example, a highly discriminant feature for user recognition that can be obtained from a sensor is the distribution of orientations of the personal care device 10 with regard to gravity during the use session. Referring to FIG. 4, in one embodiment, the device's orientation with regard to gravity can be represented by two angles ($\theta$ and $\varphi$) where the point G represents the measurement of the gravity vector in the device's local coordinate system as provided by the sensor.

Once the orientation angles $\theta$ and $\varphi$ have been computed for the entire use session, their joint probability distribution can be estimated for example with a normalized 2D histogram. For example, the angle distributions for first user may be significantly different from the distribution for a second user, indicating that they can be used to identify the user. The value in each bin of the histograms can be seen as a feature for classification.

According to an embodiment, features related to motion patterns can also be extracted from sensor data. For example, gyroscope measurements comprising angular velocity for use sessions of different users can be exploited for user identification. Examples of discriminant features include but are not limited to: (i) the standard deviation or variance of the gyroscope measurements during the use session; (ii) the number of peaks present in the signals; (iii) the average height and width of the peaks in the signal; and/or (iv) energy present in certain frequency bands as measured after applying a Fourier transform or other analysis.

According to an embodiment, if other sensors are present in the device, other discriminant features may be extracted. Among these features are, for example: (i) average force applied to the device during the use session, if a force sensor is present; (ii) time of the use session, if the device has a clock capable of determining time of the day; (iii) proximity patterns during the use session, if the device has a proximity sensor such as a capacitive or optical sensor; (iv) facial features commonly used for face recognition if the device contains a camera; and/or (v) duration of the use session, among other features.

At optional step 325 of the method, the extracted features are stored in a database such as memory 34. Alternatively, the extracted features are stored remotely from the device in a remote server, database, or other storage unit. According to an embodiment, the system may store data about a plurality of use sessions before proceeding to a downstream step, or may analyze data from a single use session upon completion, and/or may analyze data in real-time.

At optional step 326 of the method, the dimensionality module reduces the number of extracted features from one or more of the personal care sessions. According to an embodiment, the number of features extracted from the obtained sensor data can potentially be very large. For example, 2D orientation histograms may represent thousands of features depending on the chosen angle resolution. However, training a predictive model from a high dimensional feature space—using a large number of features—with a limited number of training samples may cause poor predictive performance. Accordingly, utilizing the dimensionality module to reduce the number of extracted features improves the speed and functionality of the processor and the method.

According to an embodiment, the dimensionality reduction step is optionally performed in order to reduce the total number of features prior to classification. Many techniques for dimensionality reduction could in principle be used such as principal component analysis (PCA), linear discriminant analysis (LDA), and/or Isomap, although many other dimensionality reduction methods are possible. According to an embodiment, some form of regularization may be required due to the small sample size used.

According to an embodiment, the dimensionality module 230 utilizes a regularized version of LDA or PCA followed by LDA. When utilizing a linear technique such as PCA or LDA, the dimensionality reduction step is a matrix multiplication according to the following equation:

$$\tilde{x} = W \times x \qquad \text{Eq. 1}$$

where x is the original feature vector with dimension P×1 where P is the original number of features, W is the dimensionality reduction matrix with dimensions R×P where R<<P, and $\tilde{x}$ is the reduced feature vector with dimension R×1 where R is the reduced number of features.

According to an embodiment, during the training phase, the matrix is estimated from the training database according to some criteria. During the deployment phase, the matrix is used to reduce the dimensionality of the features according to Eq. 1.

At step 328 of the method the classifier is trained, using the extracted plurality of features, to identify a characteristic of each of the at least two different users of the personal care device. According to an embodiment, once the training database is created a predictive model can be trained using machine learning algorithms such as support vector machines, K-nearest neighbors, logistic regression, and/or decision trees, among many other possible machine learning algorithms. During the training phase, the predictive model can be used to identify the regions of the feature space that should be associated with each user. Once these regions are identified, anonymous data can be classified as belonging to a specific user during the deployment phase.

According to an embodiment, the more data that is collected during the training phase, the greater the performance of the classifier. However, it is also advantageous to make the training phase as short as possible to reduce the burden on the user, since the user may have to provide an identification during the training phase. Therefore, there may be a trade-off between performance vs convenience for the user in some embodiments. Accordingly, the training phase can be designed to minimize training sessions while still achieving the desired level of performance. According to an embodiment, the number of training sessions could be chosen to depend on the number of users sharing the same device, since more data will be required to achieve a certain performance level as more users share the same device.

At this stage, the personal care device or a system or device in communication with the personal are device comprises a classifier configured to identify a characteristic of a user of the device during a subsequent personal care session. For example, the classifier of the device or system may be configured to identify which of a plurality of users are using the device. The classifier of the device or system may be configured to identify an operating characteristic of the user, including that the user is pressing too hard or too gently, among many other characteristics.

At step 330 of the method, in the deployment phase, the personal care device obtains sensor data from sensor 28 for a new personal care session by a currently unknown user of the device. The currently unknown user, however, is one of the users that provided personal care session data during the training phase. The sensor may communicate the obtained sensor to the controller and/or the extraction module. The sensor data may be used immediately or may be stored or otherwise queued for later analysis.

At step 340 of the method, the extraction module extracts a plurality of features from the new personal care session according to any of the methods or processes described or otherwise envisioned herein. For example, the extraction module may extract one or more features from the sensor data depending on, for example, the sensors present in the device.

At optional step 350 of the method, the dimensionality module reduces the number of extracted features from the new personal care session according to any of the methods or processes described or otherwise envisioned herein. For example, the dimensionality module may reduce the number of extracted features using a technique such as principal component analysis (PCA), linear discriminant analysis (LDA), and/or Isomap, although many other dimensionality reduction methods are possible. At optional step 350, the dimensionality module reduces the number of extracted features from the new cleaning session by applying to the new data the same transformation that was derived during the training phase at step 326.

At step 360 of the method, the trained classifier utilizes the extracted features to identify one or more characteristics of the previously-unidentified user of the personal care device. The characteristic may be an identity of the user, or it may be a use parameter of the user and/or the personal care session. For example, the characteristic may be information about how hard the user is pressing, among other characteristics. According to an embodiment, the classifier compares the one or more extracted features to the feature space created during the training phase, and identifies which user data the new personal care session data most closely matches.

At optional step 370 of the method, the system utilizes the identified one or more characteristics to associate the sensor data obtained during the personal care session with the identified user. This may be utilized, for example, to evaluate one or more parameters of the user's personal care session. Alternatively, this may be utilized to perform additional training of the classifier.

At optional step 380 of the method, the system utilizes the identified one or more characteristics to provide feedback to the user or a third party. For example, the system may notify the user that the personal care device has attached a head member that is associated with a different user. As another example, the system may notify the user that the user is pressing harder or softer than normal. According to an embodiment, the identification of a user may be utilized to assess the risk profile for a user that shares a device with other users, and/or to prevent a user from improperly asserting that they performed a personal care session when it was actually another user. This may be used by dental insurance providers, for example. Many other examples are possible.

At optional step 390 of the method, the system may utilize the identified one or more characteristics to modify one or more parameters or settings of the device. For example, the device may be comprise programming that indicates that the user prefers a certain setting during a personal care session, and can utilize the identification of the user to automatically activate that setting. As another example, the device may recognize that based on the user identification and a signal from the head member, that a new head member has been installed for that user. That may trigger a timer or use count related to that head member. Many other modifications or settings of the device are possible.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A method for identifying a characteristic of a user of a personal care device, the method comprising the steps of:
    providing a personal care device comprising a sensor, a controller, and a database;
    training the personal care device with training data, comprising the steps of: (i) obtaining, via the sensor, sensor data for at least one personal care session for each of at least two different users of the personal care device; (ii) extracting, via an extraction module of the processor, a plurality of features from each of the personal care sessions; (iii) reducing, using a dimensionality reduction process, the number of extracted plurality of features from one or more of the personal care sessions; and (iv) training, using the reduced number of extracted plurality of features, a classifier to identify a characteristic of each of the at least two different users of the personal care device;
    obtaining, via the sensor, sensor data for at least part of a new personal care session initiated by one of the at least two different users of the personal care device;
    extracting a plurality of features from the sensor data for the new personal care session; and
    identifying, using the trained classifier and the extracted plurality of features from the new personal care session, a characteristic of the user of the personal care device, wherein the identified characteristic of the user is an identification of the user and/or the wherein the identified characteristic of the user is an operating parameter of the user.

2. The method of claim 1, wherein the comprises one or more of principal component analysis (PCA), linear discriminant analysis (LDA), and isomap.

3. The method of claim 1, further comprising the step of associating at least some of the sensor data obtained during the new personal care session with the identified characteristic of the user.

4. The method of claim 1, further comprising the step of providing, based on the identified characteristic, feedback to the user or a third party.

5. The method of claim 1, further comprising the step of modifying, based on the identified characteristic, a parameter of the personal care device.

6. The method of claim 1, wherein the identified characteristic of the user is an identification of the user.

7. The method of claim 1, wherein the identified characteristic of the user is an operating parameter of the user.

8. The method of claim 1, wherein the classifier comprises a predictive model.

9. The method of claim 1, wherein the sensor is an inertial measurement unit.

10. A personal care device configured to identify a characteristic of a user of the device, comprising:
a sensor configured to obtain sensor data for a plurality of personal care sessions; and
a controller comprising a training module and a classifier, the training module configured to: (i) receive, from the sensor, sensor data for at least one personal care session for each of at least two different users of the personal care device; (ii) extract, via an extraction module of the processor, a plurality of features from each of the personal care sessions; (iii) reduce, using a dimensionality reduction process, the number of extracted plurality features from one or more of the personal care sessions; and (iv) train, using the reduced number of extracted plurality of features, a classifier to identify a characteristic of each of the at least two different users of the personal care device;
wherein the controller is further configured to receive, from the sensor, sensor data for at least part of a new personal care session initiated by one of the at least two different users of the personal care device, and extract a plurality of features from the sensor data for the new personal care session;
wherein the classifier is configured to identify, using the extracted plurality of features from the new personal care session, a characteristic of the user of the personal care device, wherein the identified characteristic of the user is an identification of the user and/or the wherein the identified characteristic of the user is an operating parameter of the user.

11. The personal care device of claim 10, wherein the dimensionality reduction process is further configured to reduce the number of extracted plurality of features from the new personal care session prior to the identifying step.

12. The personal care device of claim 10, wherein the controller is further configured to provide, based on the identified characteristic, feedback to the user.

13. The personal care device of claim 10, wherein the controller is further configured to modify, based on the identified characteristic, a parameter of the personal care device.

14. The personal care device of claim 10, wherein the identified characteristic of the user is an identification of the user and/or an operating parameter of the user.

15. The personal care device of claim 10, wherein the classifier comprises a predictive model.

16. The personal care device of claim 10, wherein the dimensionality reduction process comprises one or more of principal component analysis (PCA), linear discriminant analysis (LDA), and isomap.

17. A personal care device configured to provide feedback to an identified user, comprising:
a sensor configured to obtain sensor data for a plurality of personal care sessions; and
a controller comprising a training module and a classifier, the training module configured to: (i) receive, from the sensor, sensor data for at least one personal care session for each of at least two different users of the personal care device; (ii) extract, via an extraction module of the processor, a plurality of features from each of the personal care sessions; (iii) reduce, using a dimensionality reduction process, the number of extracted plurality of features from one or more of the personal care sessions; and (iv) train, using the reduced number of extracted plurality of features, a classifier to identify a characteristic of each of the at least two different users of the personal care device; and wherein the controller is further configured to: (v) receive, from the sensor, sensor data for at least part of a new personal care session initiated by one of the at least two different users of the personal care device; (vi) extract a plurality of features from the sensor data for the new personal care session; (vii) identify, using the extracted plurality of features from the new personal care session, a characteristic of the user of the personal care device, wherein the identified characteristic of the user is an identification of the user and/or wherein the identified characteristic of the user is an operating parameter of the user; and
a user interface configured to provide, based on the identified characteristic of the user of the personal care device, feedback to the user.

18. The personal care device of claim 17, wherein the dimensionality reduction process comprises one or more of principal component analysis (PCA), linear discriminant analysis (LDA), and isomap.

19. The personal care device of claim 17, wherein the feedback comprises a notification that a component of the personal care device is associated with another user of the personal care device.

20. The personal care device of claim 17, wherein the feedback comprises the identification of the user of the personal care device.

* * * * *